US012723964B2

(12) United States Patent
Miarelli

(10) Patent No.: US 12,723,964 B2
(45) Date of Patent: Sep. 1, 2026

(54) PROCESS FOR IDENTIFYING A SUB-SAMPLE AND A METHOD FOR DETERMINING THE PETROPHYSICAL PROPERTIES OF A ROCK SAMPLE

(71) Applicant: ENI S.P.A., Rome (IT)

(72) Inventor: Marco Miarelli, San Donato Milanese (IT)

(73) Assignee: ENI S.P.A., Rome (IT)

( * ) Notice: Subject to any disclaimer, the term of this patent is extended or adjusted under 35 U.S.C. 154(b) by 431 days.

(21) Appl. No.: 18/256,007

(22) PCT Filed: Dec. 2, 2021

(86) PCT No.: PCT/IB2021/061223
§ 371 (c)(1),
(2) Date: Jun. 5, 2023

(87) PCT Pub. No.: WO2022/118234
PCT Pub. Date: Jun. 9, 2022

(65) Prior Publication Data

US 2024/0053246 A1 Feb. 15, 2024

(30) Foreign Application Priority Data

Dec. 3, 2020 (IT) ........................ 102020000029744

(51) Int. Cl.
*G06K 9/00* (2022.01)
*G01N 15/08* (2006.01)
(Continued)

(52) U.S. Cl.
CPC ......... *G01N 15/0806* (2013.01); *G01N 33/24* (2013.01); *G06V 10/443* (2022.01);
(Continued)

(58) Field of Classification Search
CPC .......... G06K 9/00; G06K 9/62; G06K 9/6218; G06K 9/46; G06V 10/44
See application file for complete search history.

(56) References Cited

U.S. PATENT DOCUMENTS 8,515,721 B2 * 8/2013 Morton .................. E21B 49/00
702/6
9,507,047 B1 * 11/2016 Dvorkin ................ G01V 5/101
(Continued)

FOREIGN PATENT DOCUMENTS

AU 2017239499 A1 * 10/2017 ............ G01N 33/24
WO WO-2015153505 A1 * 10/2015 .......... G06V 10/763
WO WO-2015153506 A1 * 10/2015 ............ G06F 18/24

OTHER PUBLICATIONS

Estimating permeability from thin sections without reconstruction: Digital rock study of 3D properties from 2D images, Nishank Saxena et al., Elsevier, 2017, pp. 79-99 (Year: 2017).*
(Continued)

*Primary Examiner* — Jayesh A Patel
(74) *Attorney, Agent, or Firm* — CANTOR COLBURN LLP

(57) ABSTRACT

A process to identify a representative sub-sample of a rock sample includes the following steps:

digitally acquiring at low resolution first 2D or 3D images of the rock sample, and by a recomposition of the first images along a direction representing a digital sample;

subdividing with a volumetric subdivision the digital sample defining 3D digital blocks having a volume of substantially similar value;

analysing each 3D digital block on the basis of key points or texture descriptors obtained elaborating said plurality of the first images on the basis of the properties or structures of the rock, identifying two or more homogeneous classes of 3D digital blocks, each homoge- (Continued)

neous class defining a portion of digital sample having 3D digital blocks equivalent to each other as to the technical characteristics of the rock; and selecting at least one representative block for each homogeneous class identified, locating and extracting a subsample from the rock sample.

11 Claims, 9 Drawing Sheets

(51) Int. Cl.

| | |
|---|---|
| ***G01N 33/24*** | (2006.01) |
| ***G06V 10/44*** | (2022.01) |
| ***G06V 10/46*** | (2022.01) |
| ***G06V 10/54*** | (2022.01) |
| ***G06V 20/64*** | (2022.01) |

(52) U.S. Cl.

CPC ............ *G06V 10/462* (2022.01); *G06V 10/54* (2022.01); *G06V 20/64* (2022.01); *G01N 2015/0846* (2013.01)

(56) References Cited

U.S. PATENT DOCUMENTS

| | | | | |
|---|---|---|---|---|
| 10,198,804 | B2 * | 2/2019 | Sungkorn ............ | G06V 10/462 |
| 10,223,782 | B2 * | 3/2019 | Sungkorn ............... | G06F 18/24 |
| 10,514,372 | B2 * | 12/2019 | De Prisco .............. | G01N 15/08 |
| 10,830,713 | B2 * | 11/2020 | Zhang ................ | G01N 23/2251 |
| 2010/0128932 | A1 | 5/2010 | Dvorkin et al. | |
| 2010/0228486 | A1 * | 9/2010 | Wu .......................... | G01V 1/30 702/17 |
| 2012/0221306 | A1 * | 8/2012 | Hurley ................... | G01V 20/00 703/6 |
| 2013/0179080 | A1 * | 7/2013 | Skalinski ............... | G01V 99/00 702/6 |
| 2013/0262028 | A1 * | 10/2013 | De Prisco .............. | G01N 33/24 702/156 |
| 2015/0331145 | A1 * | 11/2015 | Grachev ................ | G16C 99/00 703/2 |
| 2016/0307312 | A1 * | 10/2016 | Sungkorn ............. | G06T 7/0004 |
| 2017/0018096 | A1 * | 1/2017 | Sungkorn .............. | G01N 33/24 |

OTHER PUBLICATIONS

Development of a Digital Rock Physics workflow for the analysis of sandstones and tight rocks, I. Verri et al., Elsevier, 2017, pp. 790-800 (Year: 2017).*

Estimation of Petrophysical Parameters from 3D images of Carbonate Core, R. M. Sok et al., Apr. 2007, pp. 1-15 (Year: 2007).*

Digital Rock Physics, Hasan Al-Marzouqi, IEEE, 2018, pp. 121-131 (Year: 2018).*

Identifying the Representative Elementry Volume for Permeability in Heterolithic Deposits Using Numerical Rock Models, Kjetil Nordahl et al., Springer, 2008, pp. 753-771 (Year: 2008).*

Determination of petrophysical properties of sedimentary rocks by optical methods, D. Korte et al., Elsevier, 2017, pp. 72-79 (Year: 2017).*

Petrophysical properties of porous medium from Petrographic Image Analysis data, Adrian Cerepi et al., Elsevier, 2001, pp. 233-256 (Year: 2001).*

United Arab Emirates Office Action for Application No. P6001290/2023, dated Dec. 13, 2024, 9 pages.

Al-Marzouqi, "Digital Rock Physics: Using CT scans to compute rock properties", IEEE Signal Processing Magazine vol. 35, No. 2, Mar. 1, 2018, pp. 121-131.

International Search Report for International Application No. PCT/IB2021/061223, dated Mar. 3, 2022, 4 pages.

Written Opinion for International Application No. PCT/IB2021/061223, dated Mar. 3, 2022, 12 pages.

Al-Raoush R. and Papadopoulos A., 2010-Representative elementary volume analysis of porous media using X-ray computed tomography. Powder Technology 200:69-77, DOI 10.1016/j.powtec.2010.02.011.

Arthur D, Vissilvitskii S (2007) K-means++: the advantages of careful seeding. Proc of the Annual ACM-SIAM Symposium on Discrete Algorithms 8:1027-1035, DOI 10.1145/1283383.1283494.

Blunt M. et al 2013—Pore-scale imaging and modelling. Advances in Water Resources 51:197-216, DOI 10.1016/j.advwatres.2012.03.003.

Clewlow L. and Strickland C., 2000-Energy derivatives: Princing and risk management.

Mostaghimi et al., 2012—Computations of absolute permeability on micro-ct images; Mathematical Geosciences 45, 24 pages, DOI 10.1007/s1 1004-012-9431-4.

Nordahl K. and Ringrose P, 2008—Identifying the representative elementary volume for permeability in heterolithic deposits using numerical rock models. Mathematical Geosciences 40:753-771.

Parrinello CM et al, 2016—Interactive Outlier Removal: A method for Identifying Outliers in Laboratory Recalibration Studies. Clinical Chemistry 62(7):966-972 DOI 10.1373/clinchem.2016.255216.

Rousseeuw PJ, 1987—Silhouettes: A graphical aid to the interpretation and validation of cluster analysis. Journal of Computational and Applied Mathematics 20:53-65, DOI https://doi.org/10.1016/03777-0427(87)90125-7.

Verri et al. 2017—Development of a digital rock physics workflow for the analysis of sandstones and tight rocks. Journal of Petroleum Science and Engineering 156:790-800, DOI https://doi.org/10.1016/j.petrol.2017.06.053.

Saudi Arabia Office Action for Application No. 523440988, dated Jan. 14, 2025, 17 pages with translation.

* cited by examiner

1

First scanning and processing 9

Acquisition of Images of the sample at low resolution 10

Preliminary processing 11 recomposition 12

Identification of the sub-sample

Rock analysis 15 second recomposition 13

Grouping, 20 third recomposition 17

Volumetric three-dimensional subdivision 30

Selecting 40

Mapping 45

Extracting 46

Petrophysical characterisation of characteristic blocks

Second scan 51 Acquisition 55

Petrophysical digital rock analysis 57

Merging of multi-scale properties

Extension of petrophysical analysis 58

100

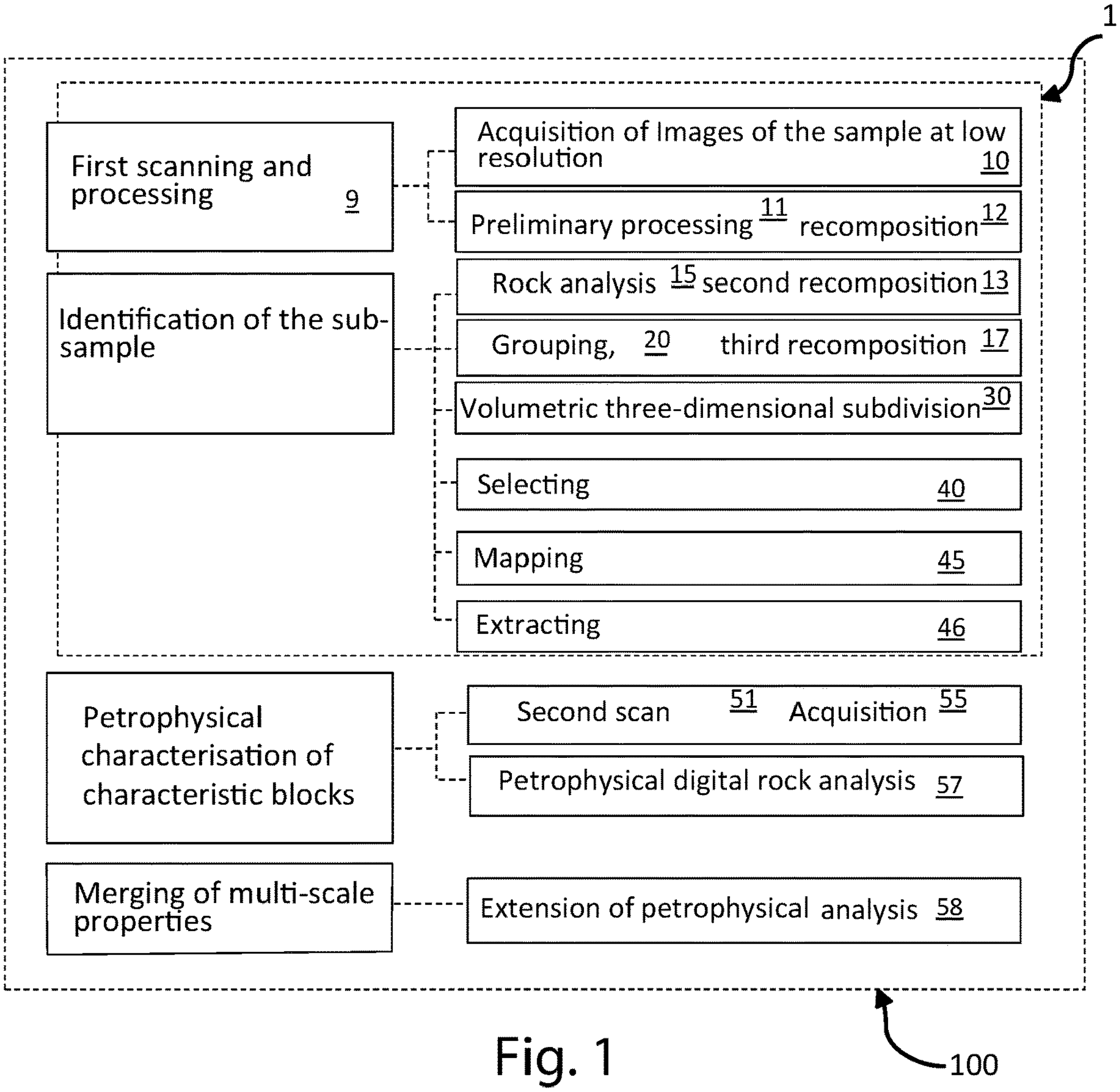

Fig. 1

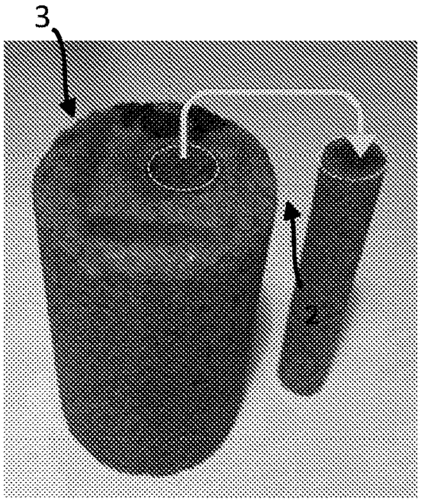

Cluster
1 Red
2 Magenta
3 Green
4 Blue
5 Yellow
6 Cyan
Silhouette Value (a)

$N_{clust}$
slice=510 Npoints=1522
Y
50 100 150 200 250 300 350 400
X
50 100 150 200 250 300 350 400

(b)

42
z
0 100 200 300 400 500 600
y
0 100 200 300 400
x
0 100 200 300 400

(a)

35
35
z
0 100 200 300 400 500 600
y
0 100 200 300 400
x
0 100 200 300 400

(b)

PROCESS FOR IDENTIFYING A SUB-SAMPLE AND A METHOD FOR DETERMINING THE PETROPHYSICAL PROPERTIES OF A ROCK SAMPLE

CROSS-REFERENCE TO RELATED APPLICATIONS

This application is a 35 U.S.C. § 371 National Stage patent application of PCT/IB2021/061223, filed on 2 Dec. 2021, which claims the benefit of Italian patent application no. 102020000029744, filed on 3 Dec. 2020, the disclosures of which are incorporated herein by reference in their entirety.

TECHNICAL FIELD

The present disclosure relates to a process for identifying at least one sub-sample representative of a rock sample.

The present disclosure further relates to a method for determining the physical or petrophysical properties of a rock sample from said at least one representative sub-sample.

BACKGROUND

As is well known, rocks have complex heterogeneous structures with wide-ranging scales. The pores, clay and organic matter that make up rocks range in size from nanometres to millimetres.

Therefore, in order to determine the petrophysical and geological properties of soils and/or deposits, rock samples are analysed using various instruments according to different methodologies. Characteristics such as porosity, relative and absolute permeability, elastic properties, pore geometry and others are examined. These characteristics make it possible to establish the fundamental structure of rock samples and the corresponding flow capacity or transport properties, thus enabling the corresponding soils and/or deposits to be explored economically. Exploration of this kind makes it possible to identify the characteristics of the soils and thus trace possible hydrocarbon deposits or extensions of existing deposits. Of course, a different evaluation of the characteristics analysed for such an exploration makes it possible to recognize deposits of water or other substances and/or to establish other properties of the soil that may be useful in related fields such as for the evaluation of the flow rate of a soil or for volcanic evaluations.

One of the tools and a process that has become standard for analysing rock samples, typically those of small (millimetric) sizes, is DRP (Digital Rock Physics), which uses two- or three-dimensional digital images. DRP is an advantageous digital technique in many respects, but requires the use of specific instrumentation. In particular, powerful image acquisition tools (microCT, X-rays) at micrometric/nanometric scales, as well as powerful computational means for storing, analysing and solving calculations with complex numerical schemes.

Additional laboratory techniques are known which, using laboratory measurements, analyse the porosity and permeability in rock samples. It should be noted that laboratory techniques are time-consuming and costly and therefore they are generally limited to small rock samples.

In particular, rock samples used for laboratory analyses are centimetric in size and are called “plugs”. Generally, plugs are rock cylinders with a diameter of 2.5 cm to 3.8 cm and a length of about 2.5 cm to 7.5 cm. Plugs are taken from the cores of larger sized or large-scale rock samples, also called core scale.

Although satisfactory in many respects, analysis using so-called laboratory techniques of plugs also has its drawbacks. Indeed, if the plugs analysed, or the sub-samples from which they are derived, are not sufficiently representative of the large-scale sample, the results obtained may identify soil characteristics that do not correspond to the actual conditions.

Other analysis techniques are also known that combine DRP with laboratory techniques and also use ML machine learning techniques which, in a multidisciplinary way, make it possible to create algorithms capable of learning from previous data appropriately stored in databases.

It is known the patent application US2016/307312A1 (Sungkorn Radompon et al) relates to a method for determining fabric of a geological sample via a multi-scale imaging for reservoir rocks.

The technical problem underlying the present disclosure is to select a sub-sample of rock which enables the technical characteristics of the original rock sample to be approximated in a simple and optimal manner, both in terms of time and instrumentation required, and which also enables the method for determining the petrophysical properties of the rock sample to be improved in terms of processing time and efficiency of the results obtained by reference to the known technique.

SUMMARY

The solution idea underlying the present disclosure is to recognize matching portions in the rock sample and to identify the sub-sample by including some parts of the matching portions.

Based on this solution idea, the technical problem is solved by a process for identifying at least one representative sub-sample of a rock sample which comprises:

- digitally acquiring at low resolution a plurality of first 2D or 3D images of the rock sample, the plurality of first 2D or 3D images being adapted to represent a digital sample of the rock sample;
- a recomposition of the plurality of first 2D images or 3D images along a direction (T) obtaining said digital sample;
  - subdividing with a volumetric subdivision said digital sample defining a plurality of three-dimensional digital blocks having a volume of substantially similar value;
  - analysing each three-dimensional digital block on the basis of a plurality of key points or texture descriptors obtained elaborating said plurality of first 2D images or 3D images on the basis of the properties or structures of the rock, and identifying two or more homogeneous classes of three-dimensional digital blocks, each homogeneous class defining a portion of digital sample having three-dimensional digital blocks equivalent to each other as to the technical characteristics of the rock;
  - selecting at least one representative block for each homogeneous class identified on said digital sample, localizing and extracting a sub-sample from said rock sample, said sub-sample comprising at least one of said representative blocks for each homogeneous class.

The process also comprises:

performing a rock analysis of the plurality of first 2D images and defining the plurality of first processed 2D images each comprising the plurality of key points or texture descriptors;

digitally processing said plurality of first processed 2D images on the basis of a digital similarity in proximity to the key points or texture descriptors and defining a plurality of first clustered 2D images wherein said key points or texture descriptors are subdivided into at least two groups of similar points;

representing said rock sample with a second digital sample superimposing, according to the direction (T), said plurality of first clustered 2D images;

performing the volumetric three-dimensional subdivision of the second digital sample defining the plurality of said 3D digital blocks.

The process also comprises:

statistically processing and subdividing said 3D digital blocks on the basis of the density of said key points or texture descriptors to define said two or more homogeneous classes of said 3D digital blocks;

extracting by a selection said one or more representative blocks from each of said two or more homogeneous classes using statistical analysis and/or filtering methods for screening said 3D digital blocks.

The process provides a preliminary processing which digitally processes said plurality of first 2D or 3D images and which determines for each first 2D or 3D image a corresponding first processed image, 2D or 3D; said rock analysis being performed on said plurality of first processed 2D or 3D images so as to define first processed 2D or 3D images comprising the key points or texture descriptors and corresponding regions of interest or volumes of interest surrounding said key points or texture descriptors, a subsequent grouping of said key points or texture descriptors, on the basis of the characteristics in said regions of interest or volumes of interest, identifies first clustered 2D images or 3D images.

The localisation provides of mapping the at least one representative block on the digital sample subdivided into said homogeneous classes and identifying by means of an affine transformation said at least one representative block in said rock sample in order to identify said sub-sample.

Advantageously, the value (V1) is determined with a statistical analysis through suitable processing and/or statistical algorithms of the characteristics identified by said similar key points or texture descriptors included in said 3D digital blocks and/or in that said value (V1) has a minimum volume value ($\mathbf{V1}_{min}$) referred to a predefined computational accuracy.

The technical problem is also solved by a method for determining the physical or petrophysical properties of a rock sample which provides for identifying and extracting from said rock sample at least one sub-sample using the process according to the present disclosure, said at least one sub-sample comprising at least one representative block for each of the two or more homogeneous classes of three-dimensional digital blocks, and digitally acquiring, at high resolution, a plurality of third digital images of said at least one sub-sample at said at least one representative block, and performing a physical or petrophysical analysis of said plurality of third digital images acquired to determine the physical or petrophysical properties the rock sample starting from the properties of the at least one representative block for each of said two or more homogeneous classes.

The technical problem is also solved by a sub-sample obtained from the process according to the present disclosure comprising at least two representative blocks having a substantially similar volume.

The technical problem is also solved by a data processing system according to claim 9 and a computer program according to claim 10.

The characteristics and advantages of the process and method according to the disclosure will become clear from the description, made below, of an embodiment given by way of non-limiting example with reference to the attached drawings.

BRIEF DESCRIPTION OF THE DRAWINGS

With reference to these figures,

FIG. 1 illustrates schematically, in a block diagram, a process and a method according to the present disclosure;

FIG. 13 schematically illustrates an original sample and a sub-sample identified by the process according to the present disclosure.

DETAILED DESCRIPTION OF THE DRAWINGS

With reference to FIG. 1, a process to identify a sub-sample 2, representative of a rock sample 3, is indicated in its entirety by the number 1. The sub-sample 2 is adapted to determine the petrophysical properties of the rock sample 3.

Figure 2A:
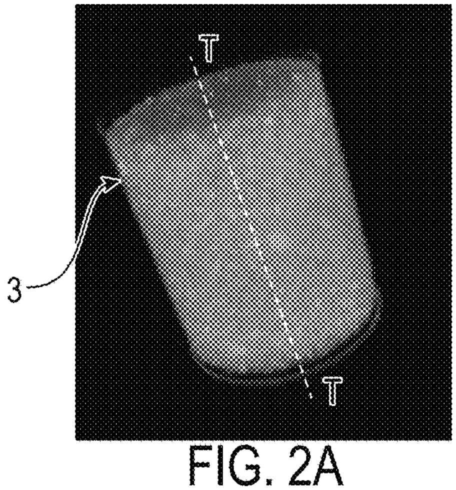
FIGS. 2 to 11 schematically illustrate a sequence of steps in the process of FIG. 1, in one embodiment.
Figure 2B:
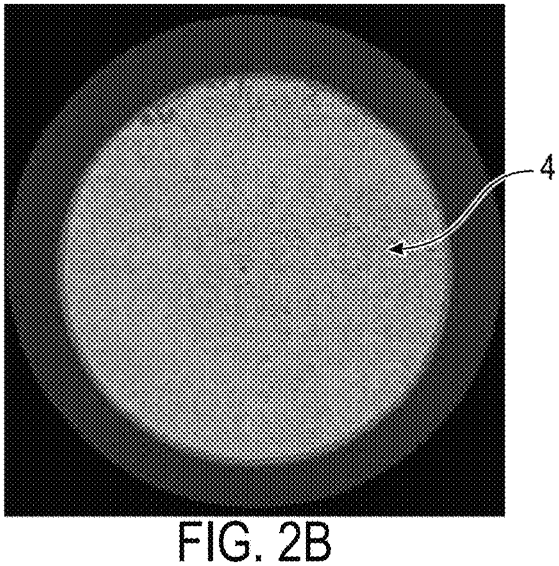
Figure 2C:
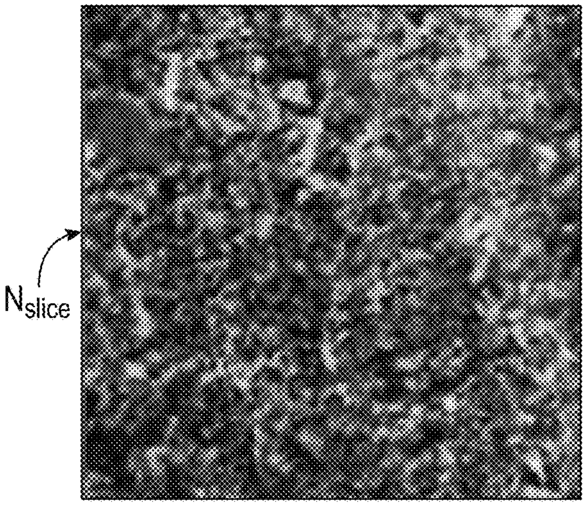

In one embodiment, the process 1 comprises a first scan 9 of the rock sample 3 to digitally acquire 10 a plurality of first images $N_{slice}$, as illustrated in FIG. 2*c*. The plurality of first images $N_{slice}$ are two-dimensional digital images and the first scan 9 is of the low-resolution, centimetre-scale type. In the present case, the digital acquisition 10 has a resolution in the range [15-40] μ-pixel. Preferably, the first scan 9 is performed on the entire rock sample 3 using a tomograph, not shown in the figures.

Each of the first images $N_{slice}$, in two dimensions, represents a corresponding slice 4 of the rock sample 3 whose height is substantially one pixel, at least in an indicative and non-limiting embodiment.

Figure 2D:
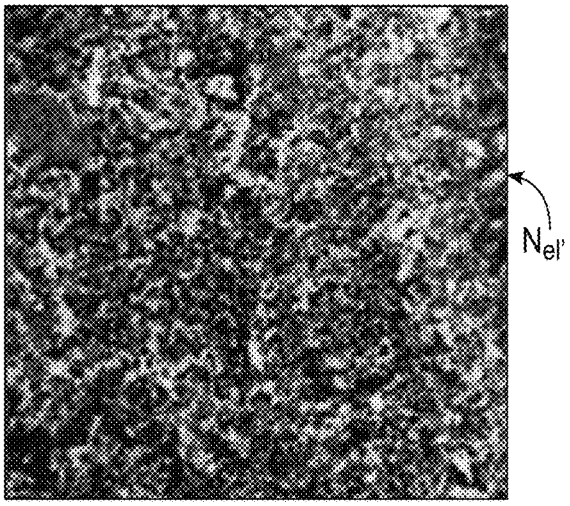
Figure 2E:
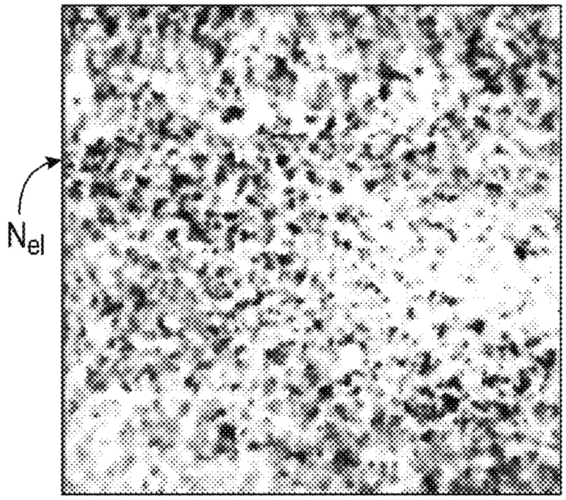
Figure 2F:
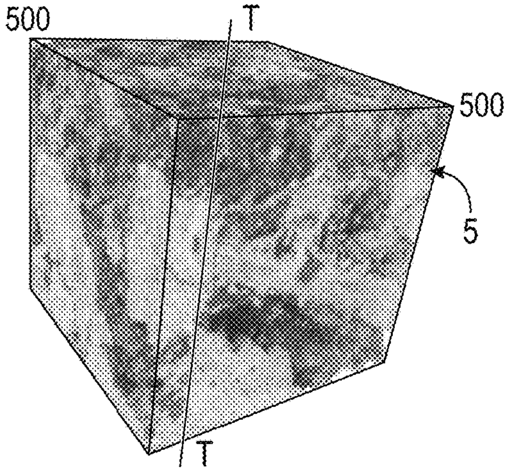

The plurality of first images $N_{slice}$ is adapted to represent a digital sample 5 of rock sample 3, as for example shown in FIG. 2*f*.

In the most general embodiment, the process 1 involves subdividing the digital sample 5 into two or more classes or homogeneous portions 33 of three-dimensional 3D digital blocks 28, as illustrated schematically in FIGS. 8*a*-8*c*. The 3D digital blocks 28 are equivalent to each other in terms of technical rock characteristics and comprise a substantially similar volume V of value V1.

Figure 11:
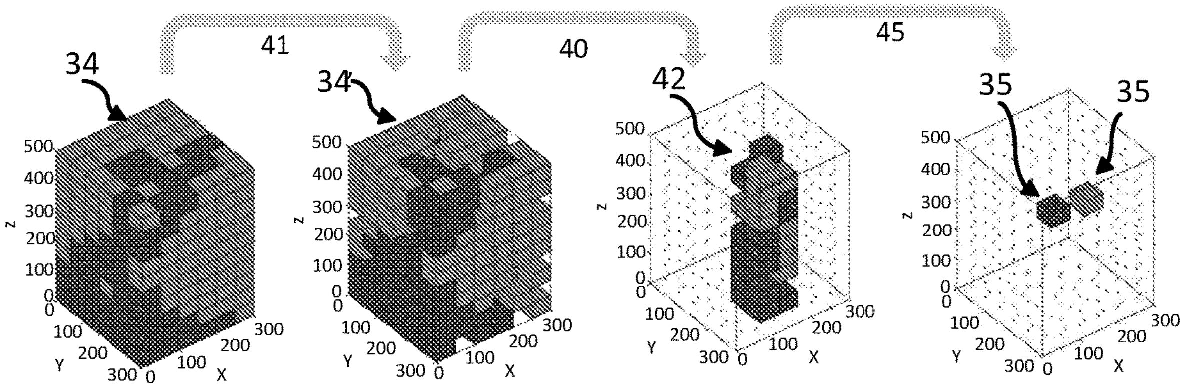

The process 1 therefore involves extracting 46 the sub-sample 2 localizing at least one representative block 35 of rock for each homogeneous class 33 identified, as shown in FIG. 11 in which two homogeneous classes have been identified.

In one embodiment, illustrated in the Figures, a preliminary processing 11 of the plurality of first images $N_{slice}$, on the basis of the digital properties, allows the removal of noise, improvement in contrast and adjust of the intensity by determining for each first image $N_{slice}$ a corresponding processed first image $N_{el}$. Preliminary processing 11 is carried out with analysis and processing software. Such software can basically be of the conventional type and known to a person skilled in the art. A result of the processing is shown in FIG. 2*e*, while FIG. 2*d* represents the processed image $N_{el}$ at an intermediate stage of processing, processed image $N_{el}'$.

Preliminary processing 11 may also involve cutting out the perimeter edges of said corresponding slice 4 obtaining for each first image $N_{slice}$ a substantially square area, as illustrated in FIG. 4*c*.

A recomposition 12 of said first processed images $N_{el}$, superimposed according to a directrix T, allows a digital sample 5 also called Cropped Digital Core Plug (CDCP) of the rock sample 3 to be obtained, as illustrated in FIG. 2*f* in a perspective view.

[[
]]

The digital sample 5 comprises a number of pixels that is defined by $$L_x^C \times L_y^C \times L_z^C$$

[[
]]

Furthermore, considering the plurality of first images processed $N_{el}$, the digital sample 5 can be represented by the expression:

$$\{M_{L_x^C \times L_y^C}\} i \in I$$

wherein $$I = \{1, \ldots, N_{slices} = L_z^C\}$$

Each first image $N_{slice}$ and each corresponding first processed image $N_{el}$ highlight rock features: pores (empty) or rock (solid) that make up each corresponding slice 4. Thus, the rock characteristics of rock sample 3 are also represented in said digital sample 5.

Subsequently, a Rock-Typing or rock analysis 15 is carried out through a digital analysis of the properties of said first processed images $N_{el}$.

Figure 3:
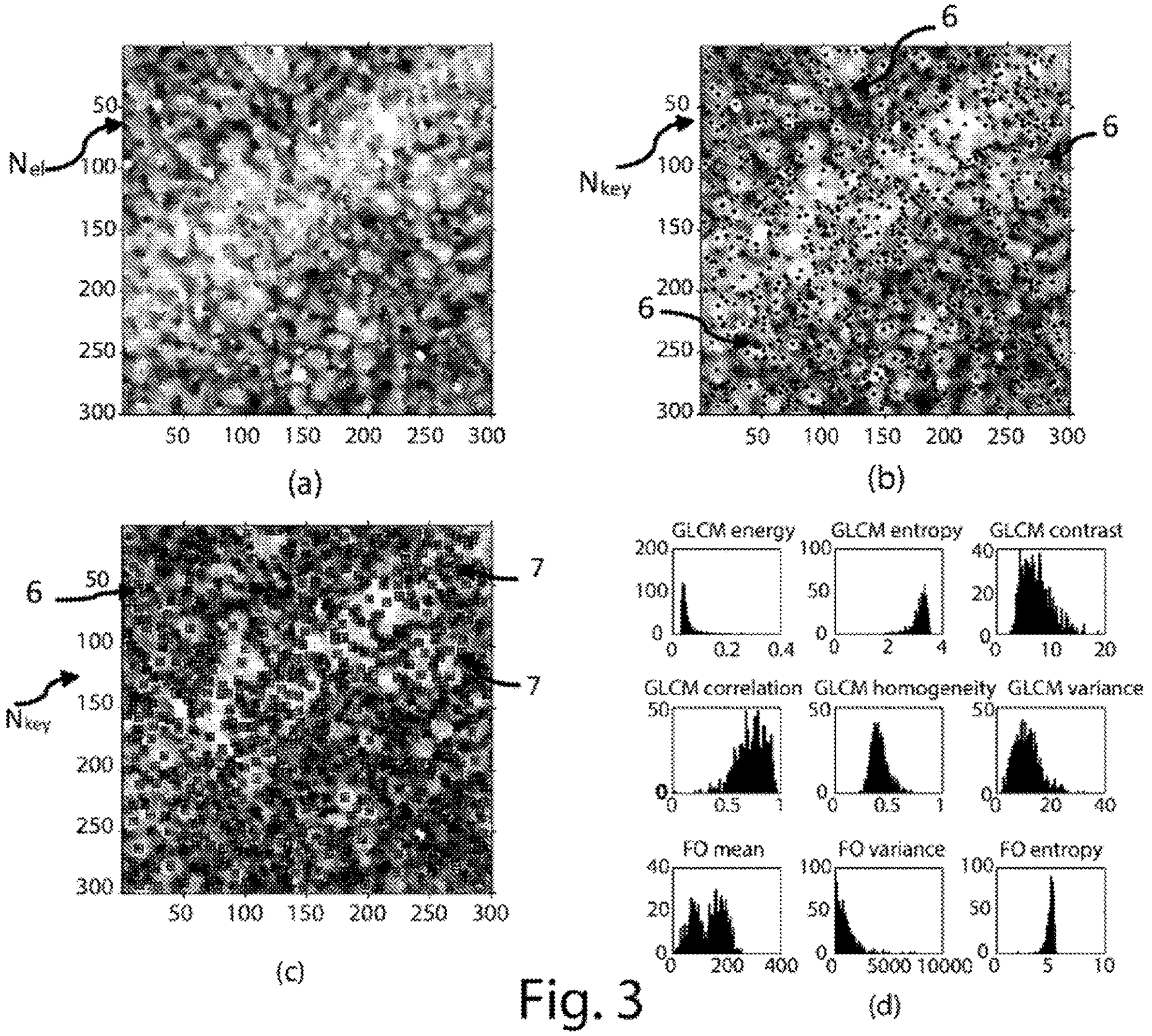

The rock analysis 15 determines a plurality of key points 6 on each first processed image $N_{el}$ and defines corresponding first processed images $N_{key}$, as illustrated schematically in FIGS. 3*a* and 3*b*. The key points 6 are texture descriptors and are defined in a variable number for each first processed image $N_{key}$.

With the use of additional processing and editing software, the key points 6 allow each first processed image $N_{key}$ to be subdivided into a plurality of regions of interest 7, as illustrated in FIG. 3*c*. Each region of interest 7 allows the identification of the rock structure and/or rock properties or characteristics in the area surrounding each key point 6.

Through processing and elaboration of each first processed image $N_{key}$, it is possible to numerically describe the properties of the rock structure at the regions of interest 7. Such properties are extracted and calculated from the characteristics of the analysed digital image. For example, analysis of appropriately defined histograms (FO) and calculation and analysis of the grey level co-occurrence matrix (GLCM). Indicatively, as schematically illustrated in FIG. 3*d*, the following values can be obtained: GLOM energy, GLCM entropy, GLCM contrast, GLCM correlation, GLCM homogeneity, GLCM variance, FO mean, FO variance, FO entropy. Then, from these values it is possible to derive the digital properties associated with the different degrees of porosity of the rock.

Figures 4A, 4B:
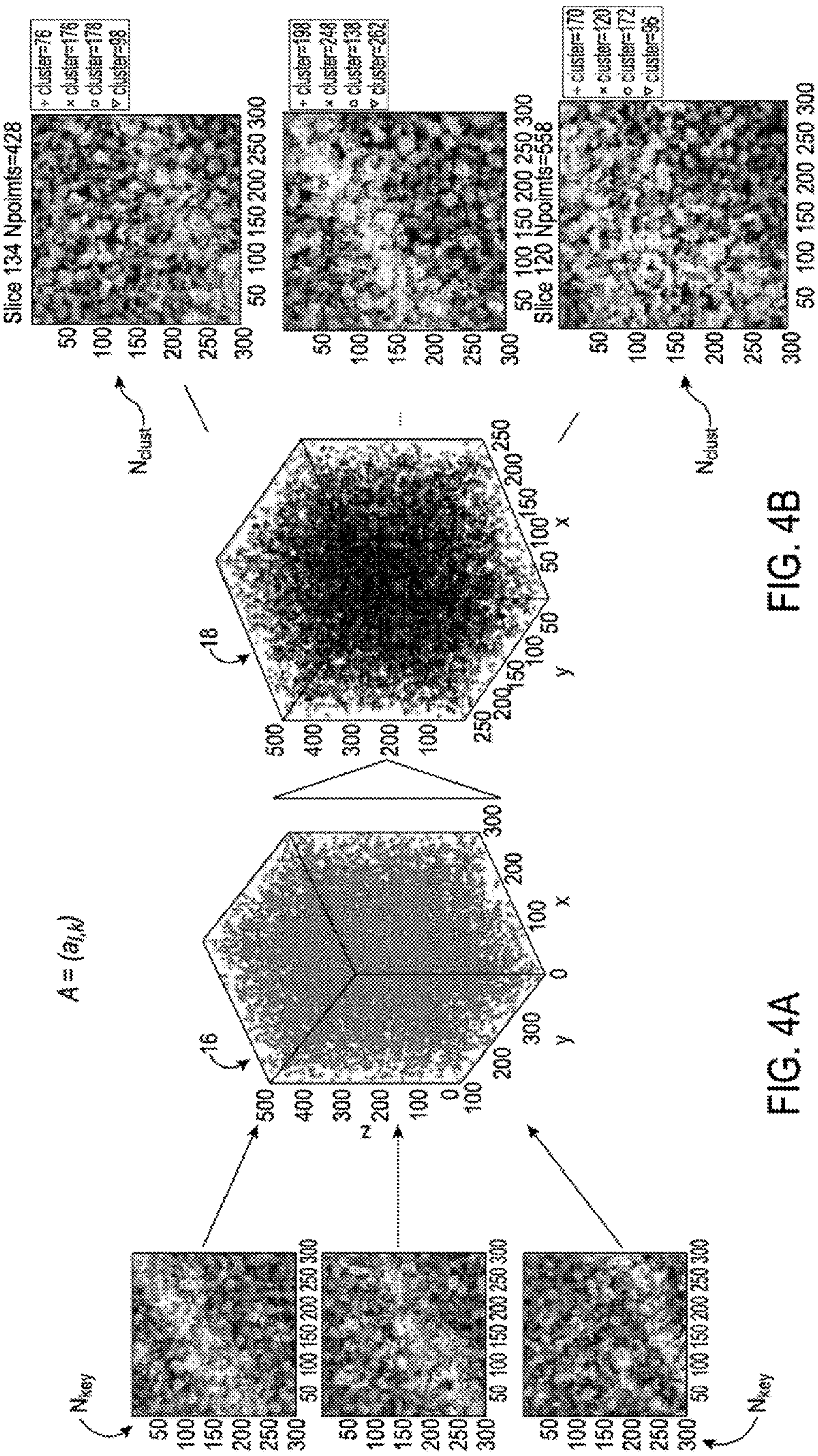

Further digital processing of said first processed images $N_{key}$, by means of a grouping or cluster 20 of said key points 6, allows the key points 6 to be subdivided into two or more groups 8 of similar points, as illustrated in FIGS. 4*a* and 4*b*. The grouping 20 is made on the basis of a similarity of the digital properties of said first processed images $N_{key}$ in the regions of interest 7 in proximity to said key points 6. With the grouping 20 each first processed image $N_{key}$ defines a first clustered image $N_{Clust}$.

In fact, each group of similar points 8 creates a link between the characteristics of the rock structure and the regions of interest 7 identifying image classes with similar or related properties.

The number of such groups 8 of similar points depends in general on the heterogeneity of the rock in said first processed images $N_{key}$.

The grouping 20, both for its execution and for the determination of the number of groups 8, uses supervised or non-supervised algorithms which, according to one embodiment, may also include machine learning methodologies. The rock analysis 15 and grouping 20, by way of non-limiting example, may use software such as Scale Invariant Feature Transform (SIFT).

A second recomposition 13 with an overlay, according to the directrix T, of the first processed images $N_{key}$ allows the rock sample 3 to be represented as a processed digital rock sample 16, illustrated in FIG. 4*a*. In one embodiment, the processed digital rock sample 16 is described by a Matrix A of the type:

[[ ]]

$$\text{Matrix } A=(a_{l,k}) \in \mathbb{R}^2$$

$$\text{Matrix } A=(a_{l,k}) \in \mathbb{R}^2$$

where k identifies the number of characteristics chosen, while the value l is obtained from the formula:

$$l = i + \sum_{j=1}^{p-1} N_{key}(j) \text{ where } i = 1, \ldots, N_{key}(p) \text{ and } p = 1, \ldots, N_{slices}$$

A third recomposition 17 of said first clustered images $N_{Clust}$, according to the directrix T, allows a second digital rock sample 18 to be defined, schematically illustrated in FIG. 4*b*.

Figure 5A:
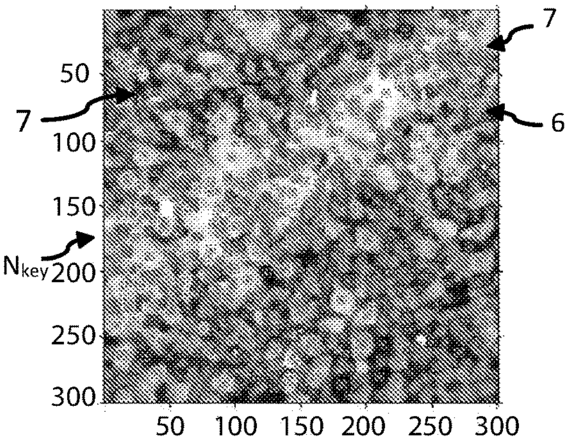
Figure 5B:
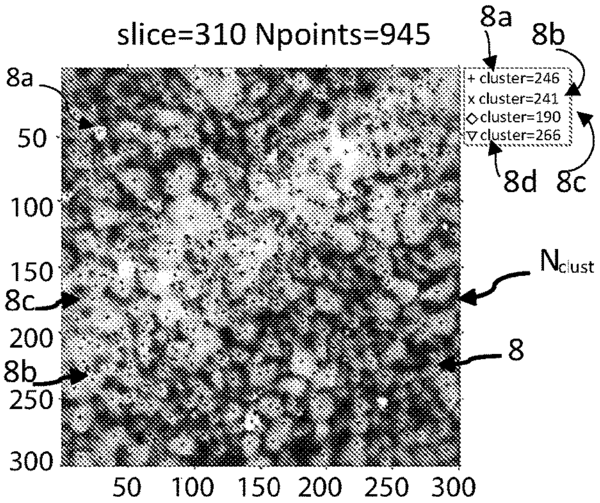
Figure 6:
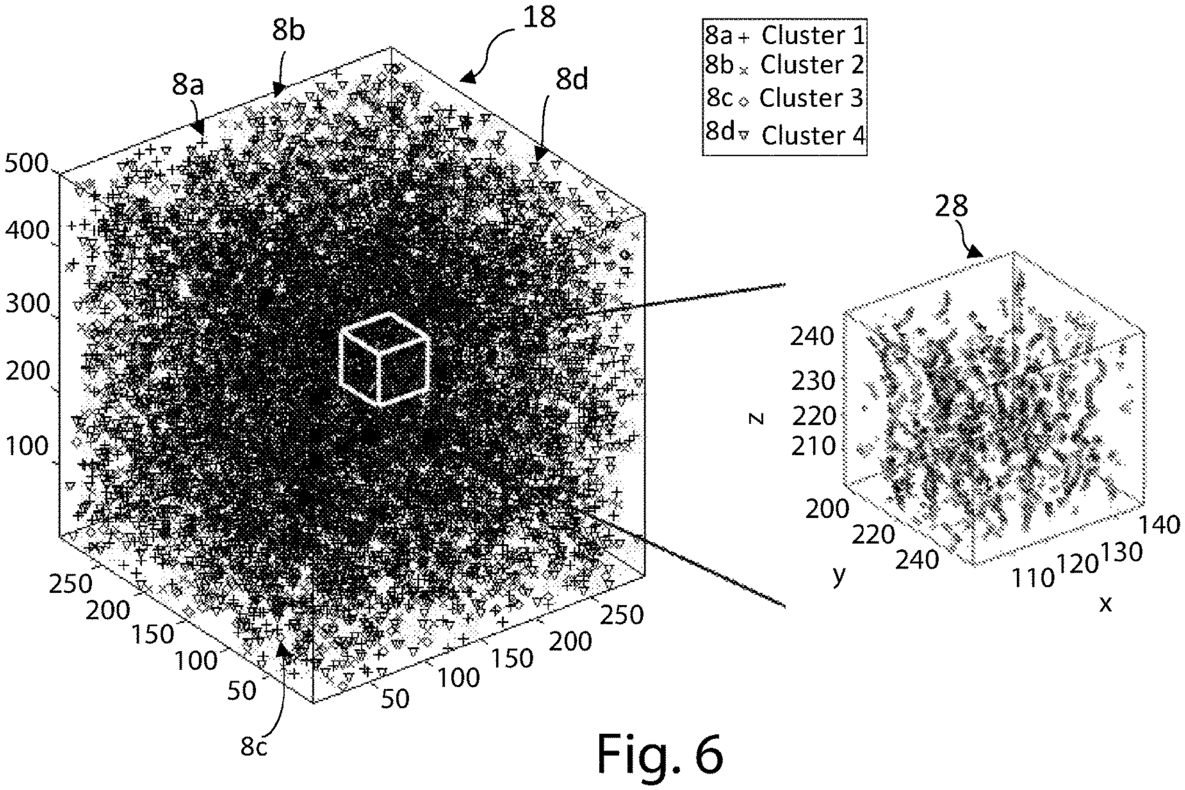

In the illustrated embodiment, the key points 6 are grouped into four groups, 8*a*-8*d*, also called clusters, as illustrated in FIGS. 4*b*, 5*b* and 6.

In the second digital rock sample 18 each group identifies related or corresponding rock classes.

Advantageously, the process 1 provides for a volumetric three-dimensional subdivision 30 of said second digital sample 18 by defining a plurality of said 3D digital blocks 28 equivalent to each other by volume V. Each 3D digital block 28 comprises a value V1 of volume V.

Preferably, the volume value V1 is determined by a statistical analysis 25 through appropriate processing and/or statistical algorithms of the characteristics identified by said groups 8a-8d of similar points included in said 3D digital blocks 28. According to an alternative embodiment, the volume value V1 is a predefined value.

Figure 7:
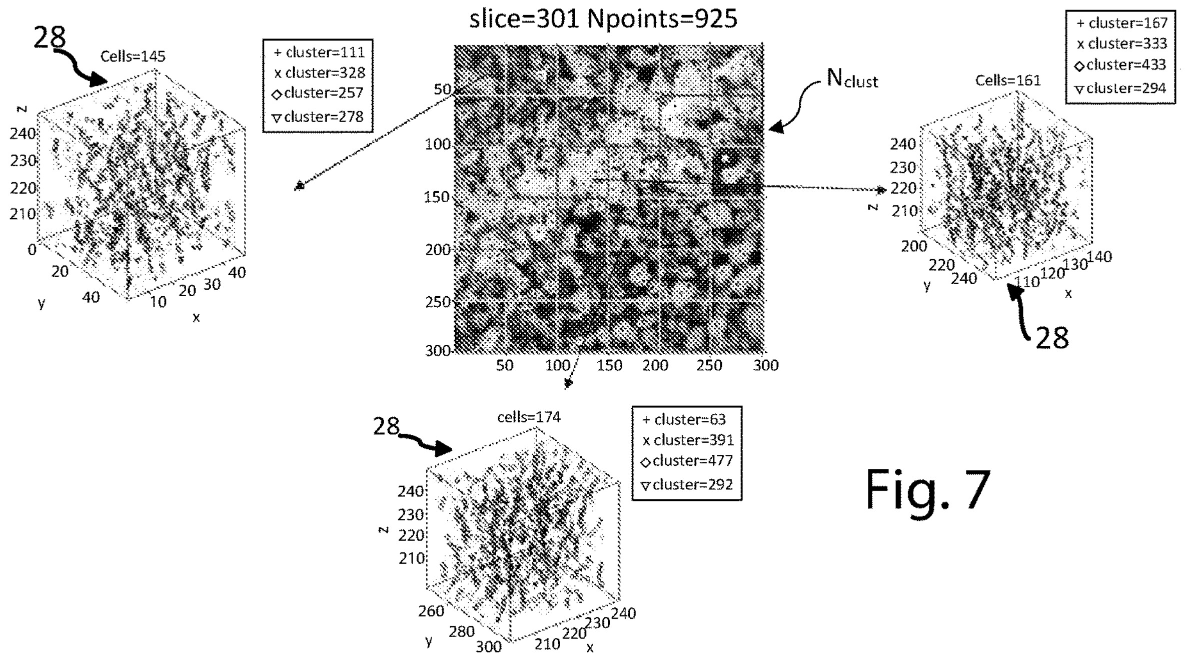

Naturally, each 3D digital block 28 of volume V1 comprises classes of two or more first clustered images $N_{Clust}$ with a different key point density 6 for each 8a-8d group, as shown in FIG. 7.

Statistical processing 32 of said plurality of 3D digital blocks 28 results in homogeneous classes 33 of blocks. The 3D digital blocks of each homogeneous class 33 have substantially similar key point densities 6 and thus, advantageously, similar rock properties i.e. similar petrophysical properties at least in the described embodiment.

[[ ]]

The rock property data as shown above of said 3D digital blocks 28 of volume V1 can be arranged in a matrix $$\text{matrix } B=(b_{n,p})\in\mathbb{R}^2,$$

Wherein:

n=1, . . . $N_{REV}$ (p) represents the number of blocks 28 that make up the second rock sample 18;

p the number of features that can be assigned to or searched for in each 3D digital block 28.

In the illustrated embodiment, by performing one or more supervised machine learning methods on the matrix B, the 3D digital blocks 28 are subdivided by defining two homogeneous classes 33a and 33b, as illustrated in FIG. 8c. According to a preferred but not limiting embodiment, the statistical processing 32 involves the use of the Kmean method (Arthur D, Vissilvitskii S (2007) K-means++: the advantages of careful seeding. Proc of the Annual ACM-SIAM Symposium on Discrete Algorithms 8:1027-1035, DOI 10.1145/1283383.1283494).

In an implementation of the process 1, the density of the key points 6 in each 3D digital block 28 of volume V1 is used as one of the statistical parameters to determine the number of homogeneous classes 33.

In addition, each 3D digital block 28 must have at least a predefined minimum Min volume value V1 necessary for computational accuracy referring quantity. According to one embodiment, the 3D digital block 28 has so-called REV dimensions for a minimum $M_{min}$ value of volume V1.

In a non-limiting example, the size of a REV block can be in the range of 0.5-1.7 $mm^3$ preferably 1 $mm^3$, or obtained according to the article by Mostaghimi et al. (2012-Computations of absolute permeability on micro-ct images; Mathematical Geosciences 45, DOI 10.1007/s1 1004-012-9431-4). Alternatively, these dimensions can be obtained according to the article by Al-Raoush R. and Papadopoulos A. (2010-Representative elementary volume analysis of porous media using X-ray computed tomography. Powder Technology 200:69-77, DOI 10.1016/j.powtec.2010.02.011) or Nordahl K. and Ringrose P (2008—Identifying the representative elementary volume for permeability in heterolithic deposits using numerical rock models. Mathematical Geosciences 40:753-771).

The rock sample 3 is then represented as a third rock sample 34 subdivided into homogeneous classes 33 of equivalent blocks appropriately interfaced with each other, as illustrated in FIGS. 8a-8c.

Figure 8:
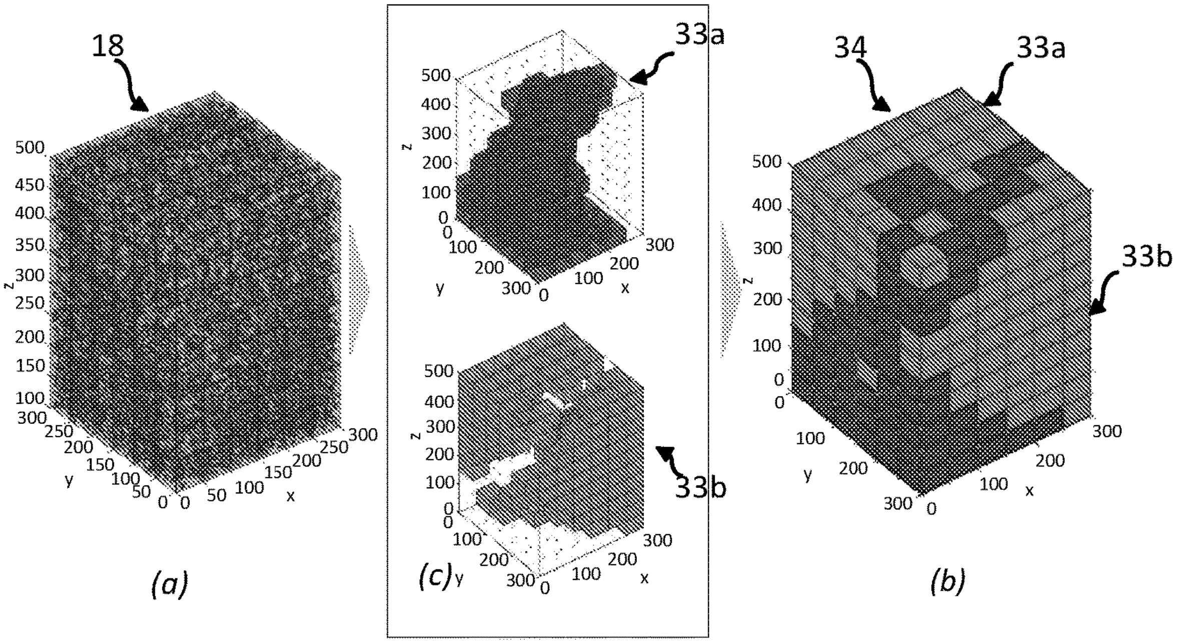

In the example shown in the intermediate frame of FIG. 8, the third rock sample 34 has two homogeneous classes, 33a and 33b, of equivalent blocks.

Figure 9:
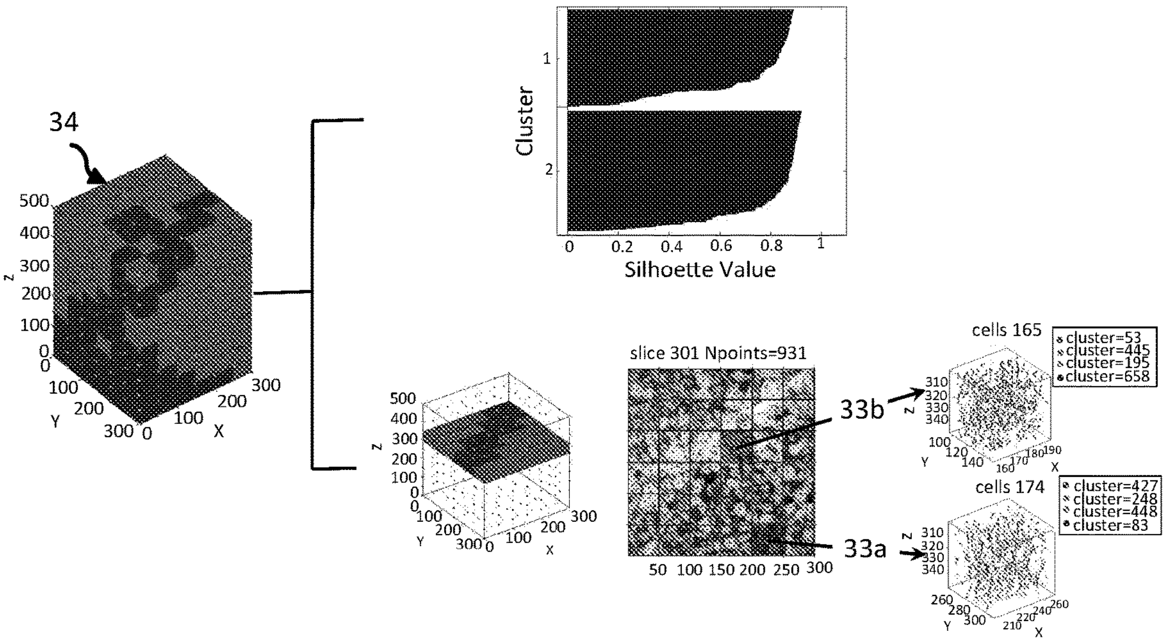

In one embodiment, it is possible to evaluate the goodness of the three-dimensional 30 volumetric subdivision and statistical processing 32 by using silhouette graphs (Rousseeuw P J, 1987—Silhouettes: A graphical aid to the interpretation and validation of cluster analysis. Journal of Computational and Applied Mathematics 20:53-65, DOI doi.org/10.1016/03777-0427(87)90125-7) and by visual comparison as shown schematically in FIG. 9.

Next, the process 1 involves selecting 40 one or more representative blocks 35 from each homogeneous class, 33a and 33b, identified.

In one embodiment, the selection 40 provides for extracting said representative blocks 35 also using statistical methodologies and/or appropriate filtering methods for further screening of said 3D digital blocks 28 allowing for improved identification.

Figure 10:
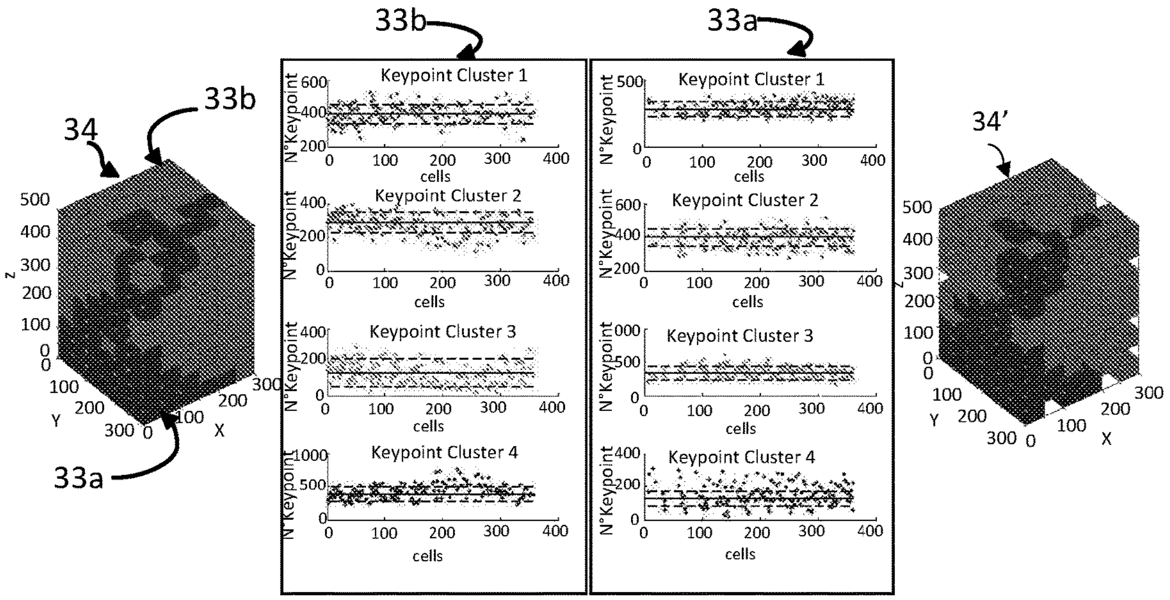

In an indicative and non-limiting embodiment, the selection 40 uses an IOR method of iterative outlier removal, illustrated schematically in FIG. 10. In FIG. 10, the solid/broken black line represents the mean/variance of convergence of the algorithm and the graphs shown are for the two homogeneous classes 33a and 33b identified.

In one embodiment, it is possible to use the IOR method as developed in "Python script" and described for example by Clewlow L. and Strickland C. (2000—Energy derivatives: Princing and risk management) and/or by Parrinello C M et al (2016—Interactive Outlier Removal: A method for Identifying Outliers in Laboratory Recalibration Studies. Clinical Chemistry 62 (7): 966-972 DOI 10.1373/clinchem.2016.255216).

In essence, the IOR method or analogues allow a screening 41 of said digital blocks-3D 28 equivalent in said homogeneous classes, 33a and 33b—and to define a third screened rock sample 34'.

According to one embodiment, the selection 40 using the IOR method involves successively:

1) measuring the mean and standard deviation of the key points 6 clustered in each equivalent block 28 belonging to a homogeneous class 33;
2) removing all the equivalent blocks 28 having a key point density 6 greater than the mean value plus two times the value of the standard deviation;
3) repeating the measurement and removal until the convergence that defines a group of candidates 42.

Subsequently, one or more groups of candidates 35 are chosen from one or more representative blocks 42 by applying further algorithms and/or based on physical constraints related to the size of the original rock sample 3 and/or related to the methodology of breaking the original rock sample 3, as schematically illustrated in FIG. 11.

Thus, mapping 45 is performed, localizing the representative blocks 35 from the group of candidates 42 in said third rock sample 34. A suitable extraction 46 allows the, extraction of a sub-sample 2, of the rock sample 3, comprising one or more representative blocks 35 for each group of candidates 42.

Figure 12:
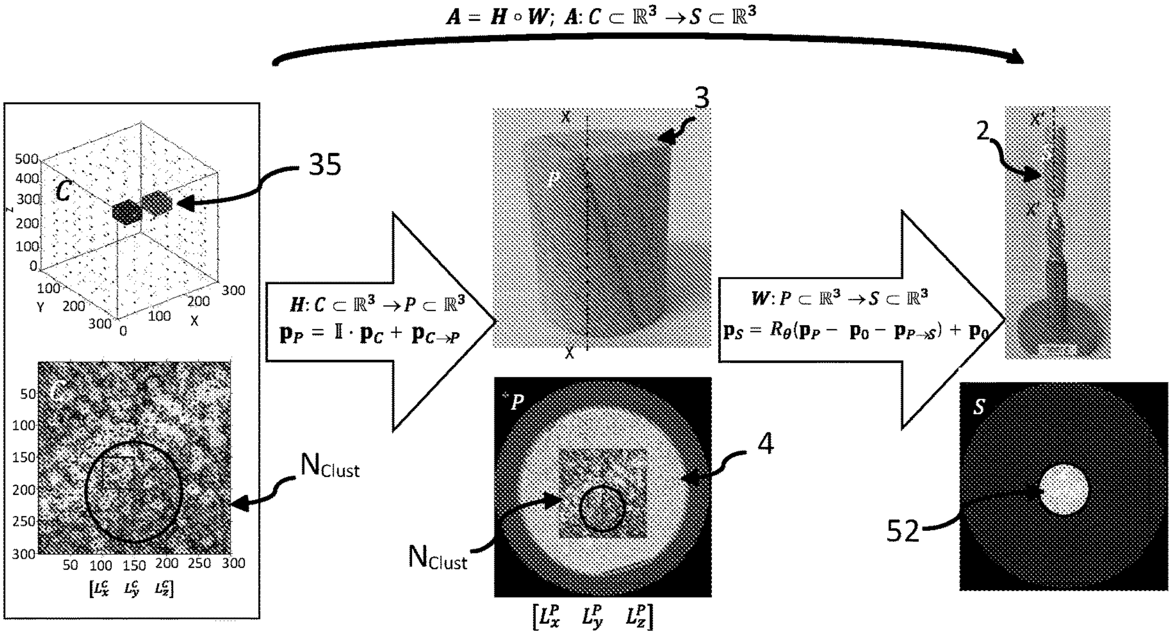
FIG. 12 schematically illustrates the identification of the sub-sample according to the present disclosure from a digital sample.

By means of an affine transformation involving a linear translation and a rototranslation, as illustrated in FIG. 12, it is possible to map 45 the sub-sample 2 with the location of one or more representative blocks 35 for each homogeneous class, 33a and 33b.

[[ ]]

In one embodiment, the affine transformation of the rock sample 3 which can be described by:

$$A=H\circ W; A:C\subset\mathbb{R}^3\rightarrow S\subset\mathbb{R}^3$$

which basically results from a combination of a linear transformation $$H:C\subset\mathbb{R}^3\rightarrow P\subset\mathbb{R}^3$$

for the transformation of the coordinates from the third rock sample 34 to the rock sample 3 according to the equation:

$$H(p_C)=p_P=T_v(p_C)$$

and then a rototranslation to transform the coordinates from the rock sample 3 to the sub-sample 2, according to the equation:

$$W(p_P)=p_s=R_\theta(p_P-p_0-p_{(P\rightarrow S)})-p_0$$

wherein $p_c=(x_c, Y_c, z_c)$ represents the coordinates of the points on a reference system relative to the third rock sample 34;

$p_s=(x_p, Y_p, z_p)$ represents the coordinates of the points on a reference system relative to the rock sample 3;

$T_v$ is the translation matrix of the component $$v=\left(0.5\times\left(L_x^P-L_x^C\right)-1,\ 0.5\times\left(L_y^P-L_y^C\right)-1,\ 0.5\times\left(L_z^P-L_z^C\right)-1.\right.$$

represents the coordinates of the points on a reference system relative to the sub-sample 2;

$$p_0=\left(L_x^P/2,\ L_y^P/2,\ L_z^P/2\right)$$

represents the coordinates of the point of origin of the rotation in the reference system relative to rock sample 3;

$p_{P\rightarrow S}=(x_{P\rightarrow S}, y_{P\rightarrow S}, z_{P\rightarrow S})$ is the vector transformation from the vector P to the vector S, θ represents the angle of rotation;

$R_\theta$ is the inverse matrix of the standard rotation.

In one embodiment, the coordinate system can be obtained through the method described by Sok R. et al. (2010-Pore scale characterization of carbonates at multiple scales: Integration of micro-ct, bsem, and fibsem. Petrophysics 51) by relating the pixels of the images defining the third rock sample 34 to the coordinates of the points in the rock sample 3. In particular, the method uses predefined base points that localize known points in the rock sample 3, as illustrated schematically in FIG. 12.

In one embodiment, the representative blocks 35 are preferably selected substantially close together due to requirements related to the operation of cutting the rock sample 3. A cylinder comprising or corresponding to said sub-sample 2 may be identified with an axis X' substantially parallel to an axis X of the rock sample 3, as illustrated in FIG. 12.

The extraction 46 of the sub-sample 2 is an invasive operation for the rock sample 3, which is cut and then destroyed. As is clear to a person skilled in the art, the process 1 could identify two or more sub-samples 2 of the rock sample 3, depending on the size of the rock sample 3 and the type of analysis required.

The process 1 as described allows the rock sample 3 to be divided into homogeneous classes or homogeneous classes 33 of blocks that are equivalent to each other in terms of technical rock characteristics and to extract the sub-sample 2 by localizing one or more representative blocks 35 of rock for each identified homogeneous class 33. It was found that the process 1 according to the present disclosure substantially and significantly reduces the processing time for identifying and extracting the sub-sample adapted to determine the petrophysical properties of the rock sample 3.

According to a further aspect of the present application, a method for determining the petrophysical properties 100 of a rock sample 3 is now described.

The method involves extracting a sub-sample 2 according to the process 1 described above, and parts and classes having the same structure and function will be given the same numbering and reference code.

A second digital scan 51 of the sub-sample 2 allows for the high-resolution digital acquisition 55 of a plurality of second digital images 52 at said representative blocks 35. In the present case, the digital acquisition 55 has a resolution in the range [1.5-2.5] μ-pixel. The digital acquisition 55 is carried out through a targeted micro-tomographic acquisition at said representative samples 35 for each homogeneous class 33.

Subsequently, a petrophysical analysis 57 of rock, of the plurality of second digital images 52 acquired allows the petrophysical properties of each representative sample 35 to be identified.

Thus, the petrophysical properties identified in said representative blocks 35 are extended 58 to the plurality of 3D digital blocks 28, according to the corresponding homogeneous class, 33*a* and 33*b*, of the third rock sample 34.

In one embodiment, the petrophysical analysis 57 of sub-sample 2 can be carried out using a so-called CFD-type solver that characterizes the micrometer-scale fluid flow details of selected samples by constructing a computational grid from 3D micrometric images (3D micro-CT images), as for example described by Blunt M. et al (2013-Pore-scale imaging and modelling. Advances in Water Resources 51:197-216, DOI 10.1016/j.advwatres. 2012.03.003) and by Mostaghimi et al. (2012).

For the determination of petrophysical properties, the presence of microporous zones plays an important role in defining the connectivity between pores and thus in determining the final permeability. Therefore, by way of non-limiting indication, in order to determine a microporosity, e.g. in the presence of porous structures with pore sizes smaller than the voxel size of the image, the petrophysical analysis 57 of the sub-sample 2 can be carried out through an algorithm described by Verri et al. (2017—Development of a digital rock physics workflow for the analysis of sandstones and tight rocks. Journal of Petroleum Science and Engineering 156:790-800, DOI doi.org/10.1016/j.petrol.2017.06.053).

Furthermore, the effect of microporosity in a representative block 35, in which porous regions can be included in the pore space, is modelled through equations that start from conservation of mass and momentum and describe the fluid-dynamic properties with increased fluid resistance. These equations are:

$$\nabla\cdot u=0 \qquad (3)$$

$$\nabla\cdot(\rho uu)=\rho g-\mu\nabla^2u+R \qquad (3)$$

Wherein:

u is the velocity of the fluid

ρ is the density of the fluid

μ is the kinematic viscosity of the fluid g is the acceleration of gravity

∇ Represents the nabla differential operator.

R is the resistivity source term calculated as the mean level of the greys corresponding to the image voxels in the microporous regions identified in said plurality of third, high-resolution, digital images 52.

According to other embodiments, the petrophysical analysis 57 may require subjective evaluations of said second digital images 52.

In one embodiment, a simulated global flow analysis 59 is applied to the second rock sample 34. According to a fluid dynamic approach, for each isothermal phase, with a steady state of the incompressible Newtonian fluid, conservation of mass and momentum is considered, and thus the fluid flowing through the porous mass is described by the Darcy equations:

$$\nabla \cdot u = 0 \tag{5}$$

$$u = -\frac{K}{\mu}(\nabla p - \rho g) \tag{6}$$

Wherein:

u is the velocity of the fluid

ρ is the density of the fluid

P is the pressure

μ is the kinematic viscosity of the fluid g is the acceleration of gravity

∇ Represents the nabla differential operator.

With the simulated global flow analysis 59 it is then possible to define the petrophysical properties of the rock sample 2.

The present disclosure also relates to a data processing system comprising a tomograph configured to perform a first digital scan 9, at low resolution, on a rock sample 3 by defining a plurality of first images $N_{slice}$. The system further comprises a processor configured to acquire said plurality of first images $N_{slice}$ and to perform the process 1 to identify a sub-sample 2 representative of a rock sample 3, as described above.

In addition, the system comprises a further tomograph configured to perform a second, high-resolution digital scan 51 of a sub-sample 2 of a rock sample 3. Said processor or a further processor being configured to perform the method 100 to determine the petrophysical properties of the rock sample 3 as described above.

Furthermore, the present disclosure comprises a computer program having instructions which, when the program is run by a computer, the computer performs the process of identifying a representative sub-sample 2 of a rock sample 3, as described above. Such program further comprising instructions such that when the program is run by a computer, the computer performs the method 100 to determine the petrophysical properties of the rock sample 3 as set forth above.

Advantageously, the process to determine the sub-sample, the method to determine the petrophysical or physical properties of the rock sample, the system and the program, as described, make it possible to compare the petrophysical or physical properties from a DRP scale to a laboratory scale in a quick and optimal way, both in terms of processing time and in terms of the instrumentation required, as is clear to a person skilled in the art.

By means of an initial low-resolution tomographic acquisition, areas of heterogeneous samples are identified guiding the choice of homogeneous classes of rock samples.

A second high-resolution tomographic acquisition allows the absolute permeability of the rock sample to be assessed from the petrophysical or physical properties measured in the individual representative samples.

In a variation of the process 1 and method according to the present disclosure, the plurality of first images $N_{slice}$ acquired from the rock sample 3 are three-dimensional or 3D images that directly define the plurality of 3D digital blocks.

The 3D digital blocks 28 thus defined are equivalent to each other in terms of technical rock characteristics and comprise a substantially similar volume V of value V1.

Process 1 is carried out as described above for 2D images, making the necessary modifications and using appropriate processing and software for 3D image analysis.

Tests Performed

Figure 14:
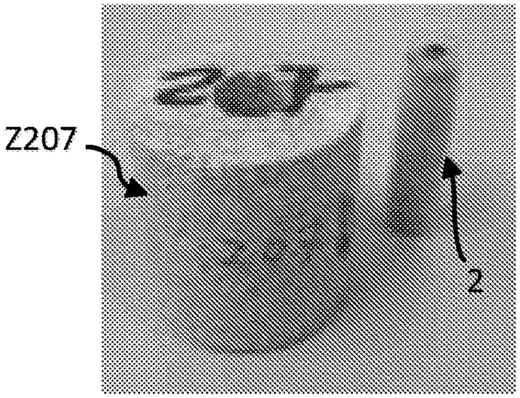
FIGS. 14 to 17 schematically illustrate certain steps and results of a test performed on a rock sample by the process and method according to the present disclosure.

It was possible to evaluate the goodness of the process and method described through some tests using a rock sample 3, called Z207, shown in FIG. 14, and the sub-sample 2 obtained through the process 1, described above.

Figure 15:
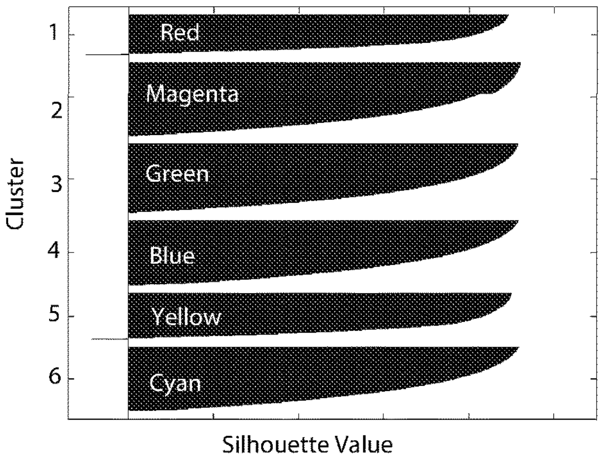
Figure 16:
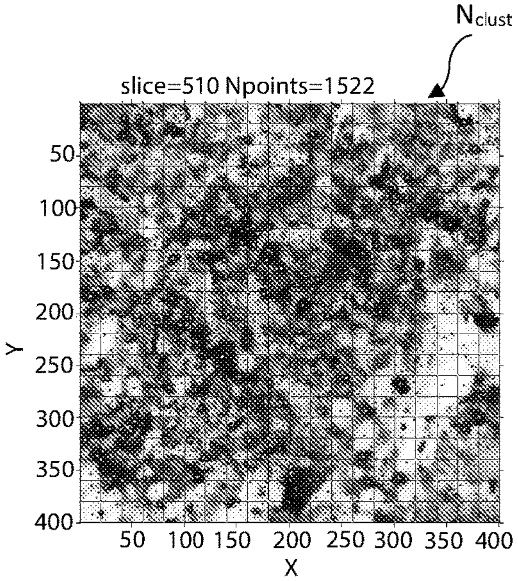
Figure 17:
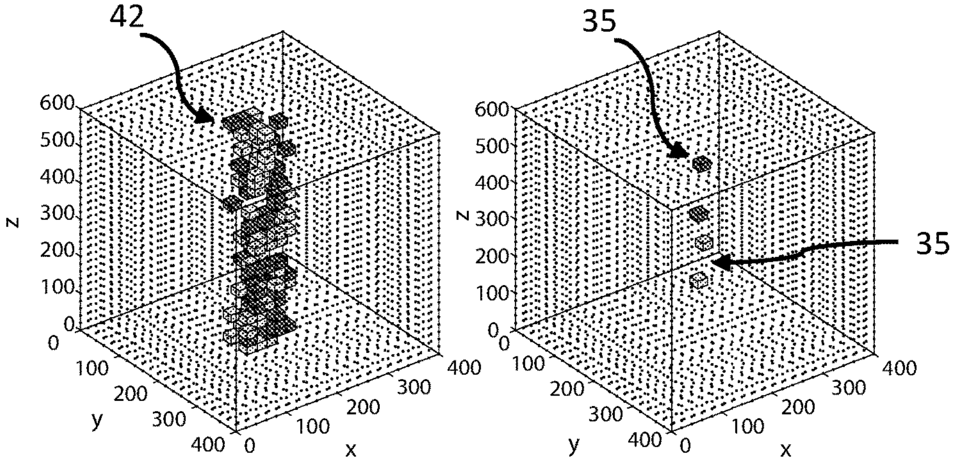

It was possible to compare the simulated flow analysis 59 on a third rock sample 34, not shown in the figures, obtained from Z207, with a real flow analysis 58. Z207 has a diameter of 38 mm and a height of 50 mm with voxel dimensions $(L_x^P \times L_x^P \times L_x^P)=(1004\times1024\times1014)$. Z207 is composed of heterogeneous carbonate rock with some fossil fragments. FIG. 15 shows some first images $N_{slice}$ of the Z207 and preliminary processing provides first processed images $N_{el}$ Of dimensions $(L_x^P \times L_x^P \times L_x^P)=(400\times400\times600)$. With the rock analysis 15 applied to the 600 images processed $N_{el}$ one at a time, the average number of key points 6 was about 1400 per image. In order to obtain a good representation of rock characteristics, the grouping 20 provides six distinct groups 8*a*-8*f* of similar points. FIG. 16 shows the analysis, with Silhouette graphs, for the six distinct groups. With the combination of FO entropy and mean FO, it is possible to estimate the pixels tones in the regions of interest 7 that surround each key point 6 of each image. A clustered image $N_{Clust}$ is shown in FIG. 17. Three-dimensional volumetric subdivision 30 subdivides the second rock sample 18 defining 12000 3D digital blocks 28 with a volume V1 of (20×20×20) voxels corresponding to (1.19×1.19) mm. An analysis of said 3D digital blocks 28, using appropriate algorithms, determined two homogeneous classes, 33*a* and 33*b*, for Z207.

The selection 40 and localization of representative blocks 35 is illustrated in FIGS. 17*a-b*.

The sub-sample 2 with a diameter of 5 mm and a length of 50 mm was obtained by extraction, illustrated in FIG. 14.

Thus, according to the method for determining the petrophysical properties, the high-resolution acquisition of the sub-sample 2 makes it possible to obtain a plurality of third images 52 from which the petrophysical properties of Z207 can be determined.

The simulated flow analysis 59 tested uses conventional methodologies such as flow-based methods, e.g. Durlofsky L (2005-Upscaling and gridding of fine scale geological models for flow simulation. Paper presented at the International Forum on Reservoir Simulation Iles Borromees, Stresa, Italy, June 20-24).

Simulated flow analysis 59 was carried out with a uniform fixed velocity at the inlet and a path flowing along a longitudinal direction of the third rock sample 34 divided into the two homogeneous classes, 33*a* and 33*b*.

The simulated analysis was compared with a real flow analysis performed on the rock sample Z207 in the Z-direction substantially perpendicular to the bearing plane of Z207. The absolute permeability values defined with the simulated flow analysis 59 are comparable with the values obtained in the laboratory with the real flow analysis 58 confirming the goodness of the process and method as described.

It has been possible to observe that the process described to identify a representative sub-sample of a rock sample achieved the predefined objects. In particular, a person skilled in the art can see how the process, method and system described allow a comparison between digital and experimental data, enabling petrophysical or physical properties to be obtained at the same scale.

It has also been observed that the process, method and system described are also suitable for use in the presence of rock samples that are deficient due to non-consolidation and/or fracture.

The invention claimed is:

1. A process for identifying a sub-sample representative of a rock sample, which comprises:

digitally acquiring at low resolution a plurality of first 2D images ($N_{slice}$, $N_{el}$) or 3D images of said rock sample, said plurality of first 2D images ($N_{slice}$, $N_{el}$) or 3D images being adapted to represent a digital sample of said rock sample;

characterised in that it comprises:

a recomposition of the plurality of first 2D images ($N_{slice}$, $N_{el}$) or 3D images along a direction (T) obtaining said digital sample;

subdividing with a volumetric subdivision said digital sample defining a plurality of three-dimensional digital blocks having a volume (V) of substantially similar value (V1);

analysing each three-dimensional digital block of the plurality of three-dimensional digital blocks on the basis of a plurality of key points or texture descriptors obtained elaborating said plurality of first 2D images ($N_{slice}$, $N_{el}$) or 3D images on the basis of properties or structures of the rock sample, and identifying two or more homogeneous classes of three-dimensional digital blocks, each homogeneous class of the identified two or more homogeneous classes defining a portion of digital sample having three-dimensional digital blocks equivalent to each other as to technical characteristics of the rock;

selecting at least one representative block for each homogeneous class identified on said digital sample, localizing and extracting a sub-sample from said rock sample, said sub-sample comprising said at least one representative blocks for each homogeneous class.

2. The process according to claim 1, further comprising:

performing a rock analysis of said plurality of first 2D images ($N_{slice}$, $N_{el}$) and defining a plurality of first processed 2D images ($N_{key}$) each comprising the plurality of key points or texture descriptors;

digitally processing said plurality of first processed 2D images ($N_{key}$) on the basis of a digital similarity in proximity to said key points or texture descriptors and defining a plurality of first clustered 2D images ($N_{Clust}$) wherein said key points or texture descriptors are subdivided into at least two groups of similar points;

representing said rock sample with a second digital sample superimposing, according to the direction T, said plurality of first clustered 2D images ($N_{Clust}$);

performing the volumetric subdivision of said second digital sample defining said plurality of three dimensional digital blocks.

3. The process according to claim 1, further including:

statistically processing and subdividing said plurality of three dimensional digital blocks on the basis of the density of said key points or texture descriptors to define said two or more homogeneous classes of said plurality of three dimensional digital blocks;

extracting by a selection said at least one representative blocks from each of said two or more homogeneous classes using statistical analysis and/or filtering methods for screening said 3D digital blocks.

4. The process according to claim 3, further including providing for a preliminary processing which digitally processes said plurality of first 2D images ($N_{slice}$) or 3D images and which determines for each first 2D image ($N_{slice}$) or 3D image a corresponding first processed 2D image ($N_{el}$) or processed 3D image, said rock analysis being performed on said plurality of first processed 2D images ($N_{el}$) or processed 3D images so as to define first processed 2D images ($N_{key}$) or processed 3D images comprising said key points or texture descriptors and corresponding regions of interest or volumes of interest surrounding said key points or texture descriptors, a subsequent grouping of said key points or texture descriptors, on the basis of the technical characteristics in said regions of interest or volumes of interest, identifies first clustered 2D images ($N_{Clust}$) or clustered 3D images.

5. The process according to claim 1, wherein the localizing comprises mapping said at least one representative block on the digital sample subdivided into said two or more homogeneous classes and identifying by means of an affine transformation said at least one representative block in said rock sample in order to identify said sub-sample.

6. The process according to claim 1, wherein said value (V1) is determined with a statistical analysis through suitable processing and/or statistical algorithms of the technical characteristics identified by said similar key points or texture descriptors included in said 3D digital blocks and/or in that said value (V1) has a minimum volume value ($V1_{min}$) referred to a predefined computational accuracy.

7. A method for determining the physical or petrophysical properties of a rock sample, the method including the following steps:

identifying and extracting from said rock sample at least one sub-sample using the process of claim 1, said at least one sub-sample comprising at least one representative block for each of the two or more homogeneous classes of three-dimensional digital blocks, digitally acquiring, at high resolution, a plurality of third digital images of said at least one sub-sample at said at least one representative block, and performing a physical or petrophysical analysis of said plurality of third digital images acquired to determine the physical or petrophysical properties of said rock sample starting from properties of said at least one representative block for each of said two or more homogeneous classes.

8. The process according to claim 1, further comprising the step of extracting the sub-sample of the rock sample having at least two representative blocks, said at least two representative blocks having the volume (V) of substantially similar value.

9. A data processing system comprising:

a first tomograph configured to perform a first digital scan at low resolution on a rock sample defining a plurality of first 2D images ($N_{slice}$) or 3D images, and a first processor configured to acquire said plurality of first 2D images ($N_{slice}$) or 3D images, and to execute the process for identifying the sub-sample representative of said rock sample according to claim 1, and comprising:

a second tomograph configured to perform a second digital scan at high resolution of the sub-sample defining a plurality of third 2D images or 3D images, and a second processor configured to execute a method for determining the physical or petrophysical properties of said rock sample, the method including the following steps:

identifying and extracting from said rock sample at least one sub-sample, said at least one sub-sample comprising at least one representative block for each of the two or more homogeneous classes of three-dimensional digital blocks, digitally acquiring, at high resolution, a plurality of third digital images of said at least one sub-sample at said at least one representative block, and performing a physical or petrophysical analysis of said plurality of third digital images acquired to determine the physical or petrophysical properties of said rock sample starting from properties of said at least one representative block for each of said two or more homogeneous classes.

10. A non-transitory memory storing a computer program, the computer program comprising instructions which when the program is executed by a computer, the computer executes the process according to claim 1.

11. A non-transitory memory storing a computer program, the computer program comprising instructions which when the program is executed by a computer, the computer executes the method according to claim 7.

* * * * *